(12) United States Patent
Kroc (10) Patent No.: US 11,717,584 B2
(45) Date of Patent: *Aug. 8, 2023

(54) SUPPORTED X-RAY HORN FOR CONTROLLING E-BEAMS

(71) Applicant: FERMI RESEARCH ALLIANCE, LLC, Batavia, IL (US)

(72) Inventor: Thomas Kroc, Batavia, IL (US)

(73) Assignee: FERMI RESEARCH ALLIANCE, LLC, Batavia, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/681,668

(22) Filed: Feb. 25, 2022

(65) Prior Publication Data
US 2022/0175981 A1 Jun. 9, 2022

Related U.S. Application Data

(63) Continuation-in-part of application No. 17/116,880, filed on Dec. 9, 2020, now Pat. No. 11,291,104, which is a continuation-in-part of application No. 16/428,664, filed on May 31, 2019, now Pat. No. 10,880,984.

(51) Int. Cl.
*A61L 2/08* (2006.01)
*H01J 37/14* (2006.01)
*H01J 37/147* (2006.01)

(52) U.S. Cl.
CPC .............. *A61L 2/087* (2013.01); *A61L 2/082* (2013.01); *H01J 37/1475* (2013.01); *H01J 2237/152* (2013.01)

(58) Field of Classification Search
CPC .............. H05H 7/04; H05H 2007/046; H05H 2007/045; H05H 2007/002; H01H 7/00
USPC ............................ 250/396 R, 397, 396 ML
See application file for complete search history.

(56) References Cited

U.S. PATENT DOCUMENTS

| 6,421,420 B1 | 7/2002 | Grodzins |
| 6,885,011 B2 | 4/2005 | Koenck et al. |
| 7,067,822 B2 | 6/2006 | Lyons et al. |

(Continued)

OTHER PUBLICATIONS

Bremsstrahlung, Wikipedia, https://en.wikipedia.org/wiki/Bremsstrahlung. Downloaded Apr. 8, 2019.

(Continued)

*Primary Examiner* — Nicole M Ippolito
(74) *Attorney, Agent, or Firm* — Loza & Loza LLP; Kevin L. Soules (57) ABSTRACT

A magnetic apparatus and a method of operating the magnetic apparatus can include a scanning electromagnet that redirects a beam of charged particles, a vacuum chamber that prevents the atmosphere from interfering with the charged particles, and, a parallelizing permanent magnet array for parallelizing the beam of charged particles. The parallelizing permanent magnet array can be located proximate to a target comprising a Bremsstrahlung target or an object that is being irradiated. The magnetic field of the scanning electromagnet can be variable to produce all angles necessary to sweep the beam of charged particles across the target and the parallelizing permanent magnet array can be configured from a magnetic material that does not require an electric current.

20 Claims, 8 Drawing Sheets

(56) References Cited

U.S. PATENT DOCUMENTS

| | | | |
|---|---|---|---|
| 8,476,602 B2 | 7/2013 | Nicolaescu et al. | |
| 8,877,472 B2 | 11/2014 | Medoff | |
| 9,960,007 B2 | 5/2018 | Matsuki et al. | |
| 9,974,974 B2 | 5/2018 | Groseth | |
| 10,188,366 B2 | 1/2019 | Beak | |
| 10,249,519 B2 | 4/2019 | Abe | |
| 10,880,984 B2 * | 12/2020 | Kroc | H05H 7/04 |
| 10,998,158 B1 | 5/2021 | Lewellen et al. | |
| 11,291,104 B2 * | 3/2022 | Kroc | H05H 7/04 |
| 2004/0079899 A1 | 4/2004 | Lijun | |
| 2007/0071167 A1 | 3/2007 | Avnery | |
| 2011/0220494 A1 | 9/2011 | Ding | |
| 2017/0268169 A1 | 9/2017 | Medoff et al. | |
| 2018/0033582 A1 | 2/2018 | Hadland | |
| 2018/0360401 A1 | 12/2018 | Lee et al. | |
| 2019/0025456 A1 | 1/2019 | Kroc et al. | |

OTHER PUBLICATIONS

Irradiation. Wikipedia, https://en.wikipedia.org/wiki/irradiation. Downloaded Apr. 8, 2019.

Popov et al. "A control system of a scanning electron pulsed beam for an industrial Linac." International Conference on Accelerator and Large Experimental Physics Control Systems,Trieste, Italy (1999).

* cited by examiner

SUPPORTED X-RAY HORN FOR CONTROLLING E-BEAMS

RELATED APPLICATION

The present application is a continuation in part of U.S. application Ser. No. 17/116,880, titled "PERMANENT MAGNET E-BEAM/X-RAY HORN," filed Dec. 9, 2020. application Ser. No. 17/116,880 is incorporated herein by reference in its entirety.

U.S. application Ser. No. 17/116,880 is a continuation in part of nonprovisional application Ser. No. 16/428,664, titled "PERMANENT MAGNET E-BEAM/X-RAY HORN," filed May 31, 2019. application Ser. No. 16/428,664 is incorporated herein by reference in its entirety.

STATEMENT OF GOVERNMENT RIGHTS

The invention described in this patent application was made with Government support under the Fermi Research Alliance, LLC, Contract Number DE-AC02-07CH11359 awarded by the U.S. Department of Energy. The Government has certain rights in the invention.

TECHNICAL FIELD

Embodiments are generally related to the field of irradiation including industrial sterilization and other irradiation processes. Embodiments further relate to magnetic devices and accelerators that produce electron beams and/or Bremsstrahlung X-rays.

BACKGROUND

Irradiation is a process by which an object may be exposed to radiation. The exposure can originate from various sources, including natural sources. Most frequently, however, the term "irradiation" relates to ionizing radiation, and to a level of radiation that will serve a specific purpose, such as sterilization and processing of materials and structures, rather than simply radiation exposure to normal levels of background radiation. The term "irradiation" usually excludes exposure to non-ionizing radiation, such as infrared, visible light, and microwaves from cellular phones or electromagnetic waves emitted by radio and television receivers and power supplies.

Irradiation can include processes such as sterilization, medical applications, ion implantation, ion irradiation, and industrial chemical applications. Irradiation can use an electron beam itself, or by way of a Bremsstrahlung converter, X-rays. X-rays may be produced by irradiating a target made of a material containing a large proportion of high atomic number atoms or ions with a suitably high-energy electron beam. Accelerating electrons across a large potential difference creating a beam of high-energy electrons and then guiding the beam to the target can produce the X-ray beam. The electrons in the electron beam interact with the electric field of the high atomic number nuclei and emit X-ray photons through the Bremsstrahlung process. The X-rays thus generated have a continuous spectrum, having an upper energy limit determined by the energy of the incident electrons.

In order to use electron beams or X-rays for industrial sterilization and other irradiation processes, the electron beam may be spread out into a curtain or a sheet. This requires a scanning magnet to sweep the electron beam back and forth to create the curtain or sheet to irradiate an item or to produce X-rays to then irradiate an item. The electrons or subsequent X-rays may remain divergent. In some cases, however, it may be more efficient and more useful in irradiation activities if the electron beam is redirected, using another magnet, to a trajectory that is parallel, but displaced from the original electron trajectory. This parallelized electron beam can then be used to either irradiate an item or to create X-rays to perform the irradiation.

Many industrial and scientific processes may require the use of radioisotopes as the source of radiation. Organizations and companies would like to reduce the dependence on radioisotopes for such processes, such as sterilization. For example, presently, sterilization using ionizing radiation relies heavily on gamma rays from the decay of Cobalt-60. A safer alternative can be found in the field of irradiation, particularly X-ray beam and electron beam applications, as discussed above. These applications, however, require electrical power to generate. Reducing electricity use and adding simplicity of operation to irradiation devices and processes may render irradiation an attractive alternative to radioisotope-type applications.

BRIEF SUMMARY

The following summary is provided to facilitate an understanding of some of the innovative features unique to the disclosed embodiments and is not intended to be a full description. A full appreciation of the various aspects of the embodiments disclosed herein can be gained by taking the entire specification, claims, drawings, and abstract as a whole.

It is, therefore, one aspect of the disclosed embodiments to provide for a magnetic apparatus for use in irradiation processes.

It is another aspect of the disclosed embodiments to provide for a magnetic apparatus that can be configured as a magnetic device that produces parallel electron beams or X-ray beams while reducing electrical requirements.

It is yet another aspect of the disclosed embodiments to provide for a magnetic apparatus that includes permanent magnets for parallelizing electron and X-ray beams, and which does not require an electric current.

It is still a further aspect of the disclosed embodiments to provide for a magnetic apparatus that incorporates permanent magnets having a magnetic field strength that is adjustable to compensate for any degradation of magnetic field strength over time.

It is also an aspect of the disclosed embodiments to provide for a magnetic apparatus that incorporates permanent magnets having a magnetic field strength that is dynamically adjustable to dynamically shape the radiation field to adapt to the needs of the requirements of the irradiation process.

The aforementioned aspects and other objectives and advantages can now be achieved as described herein.

In an embodiment, a magnetic apparatus can include a scanning electromagnet that redirects a beam of charged particles, a vacuum chamber that prevents the atmosphere from interfering with the charged particles, and a parallelizing permanent magnet array for parallelizing the beam of charged particles including any uniformly diverging beam. The parallelizing permanent magnet array can be located proximate to a target comprising a Bremsstrahlung target or an object that is being irradiated. The magnetic field of the scanning electromagnet can be variable to produce all angles necessary to sweep the beam of charged particles across the target and the parallelizing permanent magnet array can be configured from a magnetic material that does not require an electric current.

In an embodiment, the beam of charged particles can be redirected by the parallelizing permanent magnet array from a diverging pattern output from the scanning electromagnet to a parallel pattern after being subjected to the parallelizing permanent magnet array.

In an embodiment, the beam of charged particles can comprise an electron beam.

In an embodiment, the beam of charged particles can include an optional X-ray accessory after the beam of charged particles has been subject to parallelization.

In an embodiment, the parallelizing permanent magnet array can include a plurality of permanent magnets, wherein the plurality of permanent magnets is adjustable to compensate for a degradation of magnetic field strength over time.

In an embodiment, the magnetic field strength can remain constant over a period of time by adjusting a gap between magnetic pole faces of permanent magnets among the plurality of permanent magnets.

In an embodiment, the magnetic field strength can be adjustable by at least one of: adjusting a gap between at least two poles of permanent magnets in the plurality of permanent magnets; or adding, removing or moving the magnetic material, which modifies the magnetic field of the permanent magnets, wherein the magnetic material is selected based on a magnetic permeability.

In an embodiment, the magnetic apparatus can comprise an irradiation device for irradiating an object.

In another embodiment, a magnetic apparatus can include a scanning electromagnet that redirects a beam of charged particles, and a vacuum chamber that prevents the atmosphere from interfering with the charged particles. The magnetic apparatus can further include a parallelizing permanent magnet array for parallelizing the beam of charged particles including any uniformly diverging beam, wherein the parallelizing permanent magnet array is located proximate to a target comprising a Bremsstrahlung target or an object that is being irradiated. A magnetic field of the scanning electromagnet can be variable to produce all angles necessary to sweep the beam of charged particles across the target and the parallelizing permanent magnet array can be configured from a magnetic material that does not require an electric current. The beam of charged particles can be redirected by the parallelizing permanent magnet array from a diverging pattern output from the scanning electromagnet to a parallel pattern after being subjected to the parallelizing permanent magnet array.

In an embodiment, a method of operating a magnetic apparatus can involve redirecting a beam of charged particles with a scanning electromagnet that engages a vacuum chamber that prevents the atmosphere from interfering with the charged particles; and parallelizing the beam of charged particles including any uniformly diverging beam with a parallelizing permanent magnet array, wherein the parallelizing permanent magnet array is located proximate to a target comprising a Bremsstrahlung target or an object that is being irradiated, wherein a magnetic field of the scanning electromagnet is variable to produce all angles necessary to sweep the beam of charged particles across the target and wherein the parallelizing permanent magnet array is configured from a magnetic material that does not require an electric current.

An embodiment of the method can further involve redirecting the beam of charged particles by the parallelizing permanent magnet array from a diverging pattern output from the scanning electromagnet to a parallel pattern after being subjected to the parallelizing permanent magnet array.

In an embodiment of the method, the beam of charged particles can comprise an electron beam.

In an embodiment of the method, the beam of charged particles can comprise an X-ray portion after the beam of charged particles has been subject to parallelization.

In an embodiment of the method, the parallelizing permanent magnet array can comprise a plurality of permanent magnets, wherein the plurality of permanent magnets is adjustable to compensate for a degradation of magnetic field strength over time.

In an embodiment of the method, the magnetic field strength can remain constant by adjusting a gap between magnetic pole faces of permanent magnets among the plurality of permanent magnets.

In an embodiment of the method, the magnetic field strength can be adjustable by: adjusting a gap between at least two poles of permanent magnets in the plurality of permanent magnets, or adding, removing or moving the magnetic material, which modifies the magnetic field of the permanent magnets, wherein the magnetic material is selected based on a magnetic permeability.

In an embodiment of the method, the magnetic apparatus can comprise an irradiation device for irradiating an object.

BRIEF DESCRIPTION OF THE FIGURES

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

DETAILED DESCRIPTION

The particular values and configurations discussed in these non-limiting examples can be varied and are cited merely to illustrate one or more embodiments and are not intended to limit the scope thereof.

Subject matter will now be described more fully herein after with reference to the accompanying drawings, which form a part hereof, and which show, by way of illustration, specific example embodiments. Subject matter may, however, be embodied in a variety of different forms and, therefore, covered or claimed subject matter is intended to be construed as not being limited to any example embodiments set forth herein; example embodiments are provided merely to be illustrative. Likewise, a reasonably broad scope for claimed or covered subject matter is intended. Among other things, for example, subject matter may be embodied as methods, devices, components, or systems/devices. Accordingly, embodiments may, for example, take the form of hardware, software, firmware or any combination thereof (other than software per se). The following detailed description is, therefore, not intended to be interpreted in a limiting sense.

Throughout the specification and claims, terms may have nuanced meanings suggested or implied in context beyond an explicitly stated meaning. Likewise, phrases such as "in one embodiment" or "in an example embodiment" and variations thereof as utilized herein do not necessarily refer to the same embodiment and the phrase "in another embodiment" or "in another example embodiment" and variations thereof as utilized herein may or may not necessarily refer to a different embodiment. It is intended, for example, that claimed subject matter include combinations of example embodiments in whole or in part.

In general, terminology may be understood, at least in part, from usage in context. For example, terms, such as "and", "or", or "and/or" as used herein may include a variety of meanings that may depend, at least in part, upon the context in which such terms are used. Typically, "or" if used to associate a list, such as A, B, or C, is intended to mean A, B, and C, here used in the inclusive sense, as well as A, B, or C, here used in the exclusive sense. In addition, the term "one or more" as used herein, depending at least in part upon context, may be used to describe any feature, structure, or characteristic in a singular sense or may be used to describe combinations of features, structures, or characteristics in a plural sense. Similarly, terms such as "a", "an", or "the", again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context. Additionally, the term "step" can be utilized interchangeably with "instruction" or "operation".

Unless defined otherwise, all technical and scientific terms used herein have the same meanings as commonly understood by one of ordinary skill in the art. As used in this document, the term "comprising" means "including, but not limited to." The term "at least one" conveys "one or more".

As discussed previously, in order to use X-rays for industrial sterilization and other irradiation processes, an electronic beam from an accelerator may be used to produce Bremsstrahlung X-rays by directing the electron beam onto the target. This can be most useful if the electron beam is spread out into a curtain or a sheet before striking the target. This may require a scanning magnet to sweep the electron beam back and forth across the target to create a curtain or sheet. The electronics and subsequent X-rays may remain divergent. In some cases, however, it may be more efficient and more useful in irradiation activities if the resulting X-ray beam is redirected, using another magnet, to a trajectory that is parallel, but displaced from the original electron trajectory.

Figure 1:
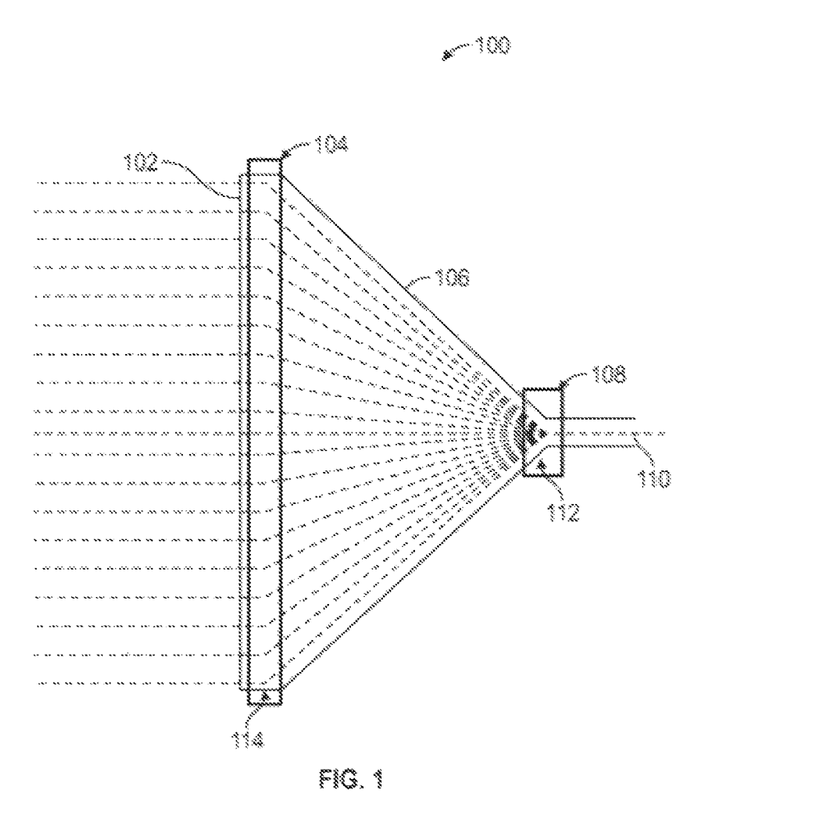
FIG. 1 illustrates a schematic diagram of a magnetic apparatus, in accordance with an embodiment.

FIG. 1 illustrates a schematic diagram of a magnetic apparatus 100, in accordance with an embodiment. The magnetic apparatus 100 can be used to produce electron beams or X-rays for irradiation processes including, but not limited to industrial sterilization and other irradiation purposes. The magnetic apparatus 100 can include a scanning electromagnet 108 and a vacuum chamber 106. The vacuum chamber 106 can include a first section 112 and a second section 114. The second section 114 can be wider than the first section 112. Note that in some example embodiments, the vacuum chamber 106 may be a cone-shaped vacuum chamber or a horn-shaped vacuum chamber referred to as a scanning horn vacuum chamber. It should be appreciated, however, that the vacuum chamber 106, although shown in FIGS. 1-3 as horn-shaped, is not limited to such a shape. Other configurations and shapes are possible. For example, the vacuum chamber 106 is shown in FIG. 4 as a rectangular or box-shaped vacuum chamber.

The scanning electromagnet 108 can be utilized to redirect a beam of charged particles. Note that from a physics perspective, there is no interaction between the scanning electromagnet 108 and the vacuum chamber 106. The "interaction" is actually between the magnetic field and the charged particles. The vacuum chamber 106 keeps the atmosphere from interfering with the charged particles. The vacuum chamber 106 can be configured from materials that are "transparent" to the magnetic field of the magnets that are external the vacuum chamber 106.

Additionally, it can be appreciated that the disclosed embodiments can be implemented for all charged particles. Electrons, however, are approximately 2000 times lighter than the next lightest particle (protons) so an implementation may be presently only practical for electrons.

A beam line 110 is also depicted in FIG. 1 with respect to the scanning electromagnet 108. A parallelizing permanent magnet array 104 is shown in FIG. 1 with respect to the vacuum chamber 106 at a second section 114 of the vacuum chamber 106, and proximate to a target 102, which may be a Bremsstrahlung target or an object that is being irradiated. (An example of an object that is being irradiated is depicted as object 116 in the alternative embodiments depicted in FIGS. 2-3.) Note that in some embodiments, the target 102 can be located in a vacuum window if operating in an electron beam mode. The target 102 can also serve in some example embodiments as both a vacuum window and a Bremsstrahlung target if operating in an X-ray mode. In still other example embodiments, the vacuum window and Bremsstrahlung target can be separate components. If separate, this allows switching between electron beam and X-ray mode by moving the Bremsstrahlung target out of the way. Note that the parallelizing permanent magnet array 104 can be located within or outside the vacuum chamber 106.

Note that as utilized herein, the term Bremsstrahlung can relate to electromagnetic radiation produced by the deceleration of a charged particle when deflected by another charged particle, typically an electron by an atomic nucleus. The moving particle loses, kinetic energy, which can be converted into radiation (e.g., a photon), thus satisfying the law of conservation of energy. The term Bremsstrahlung can also relate to the process of producing radiation. Bremsstrahlung has a continuous spectrum, which can become more intense and whose peak intensity shifts toward higher frequencies as the change of the energy of the decelerated particles increases.

It should be appreciated that the disclosed embodiments are not limited to only an X-ray mode. That is, irradiation can use either the electron beam itself or, by way of a Bremsstrahlung converter, X-rays. Thus, to be clear, the disclosed embodiments are not limited to X-rays. A Bremsstrahlung converter can be located after the permanent magnet if used in X-ray mode.

The parallelizing permanent magnet array 104 can be configured from an array of permanent magnets. Note that the strength of a scanning magnet (in this case the electromagnet 108) should be variable in order to produce all the angles necessary to sweep the beam across the target. Thus, an electromagnet may be used as a scanning magnet, which is the case with the scanning electromagnet 108. The required strength of a parallelizing magnet, however, may be proportional to the position of the electron beam from the beam line 110. For this reason, the parallelizing magnet can be configured from permanent magnet materials that do not require an electric current in the context of the parallelizing permanent magnet array 104. The strength of this permanent magnet material is arranged to provide a magnetic field that increases with distance away from the centerline. This configuration can reduce the operating costs of the magnetic apparatus 100 while facilitating the elimination of failure modes in an irradiation facility.

The magnetic apparatus 100 can produce a spatially varying magnetic field so that the electrons are redirected from a diverging pattern to a parallel pattern. That is, the beam can be redirected by the parallelizing permanent magnet array 104 from a diverging pattern output from the scanning electromagnet 108 to a parallel pattern after being subjected to the parallelizing permanent magnet array 104. In some embodiments, the parallelizing permanent magnet array 104 can be configured as an array of permanent magnets. Note that X-rays are not affected by magnetic fields. They must be generated after the electron beam has been parallelized.

Because permanent magnets may lose a few percent of their strength per year, adjustments can be provided into the magnetic apparatus 100 to allow the magnetic field strength to be made constant by adjusting the gap between magnetic pole faces. Adjusting the gap can be accomplished by adjusting the gap between the two poles of a permanent magnet. Adding, removing, or simply moving magnetic materials that modify the magnetic field of the permanent magnets that make up the parallelizing permanent magnet array 104 can also implement this adjusting operation. These materials can be selected based on their magnetic permeability and are used as shims and otherwise modify the magnetic field. In a dynamic system as disclosed herein, both permanent magnets and these magnetic materials can be mechanically manipulated to adjust the magnetic field.

The magnetic apparatus 100 can be configured as a magnetic device that produces parallel electron beams or X-ray beams while reducing electrical requirements. The aforementioned adjustments can be implemented to compensate for any degradation of magnetic field strength over time.

Figure 2:
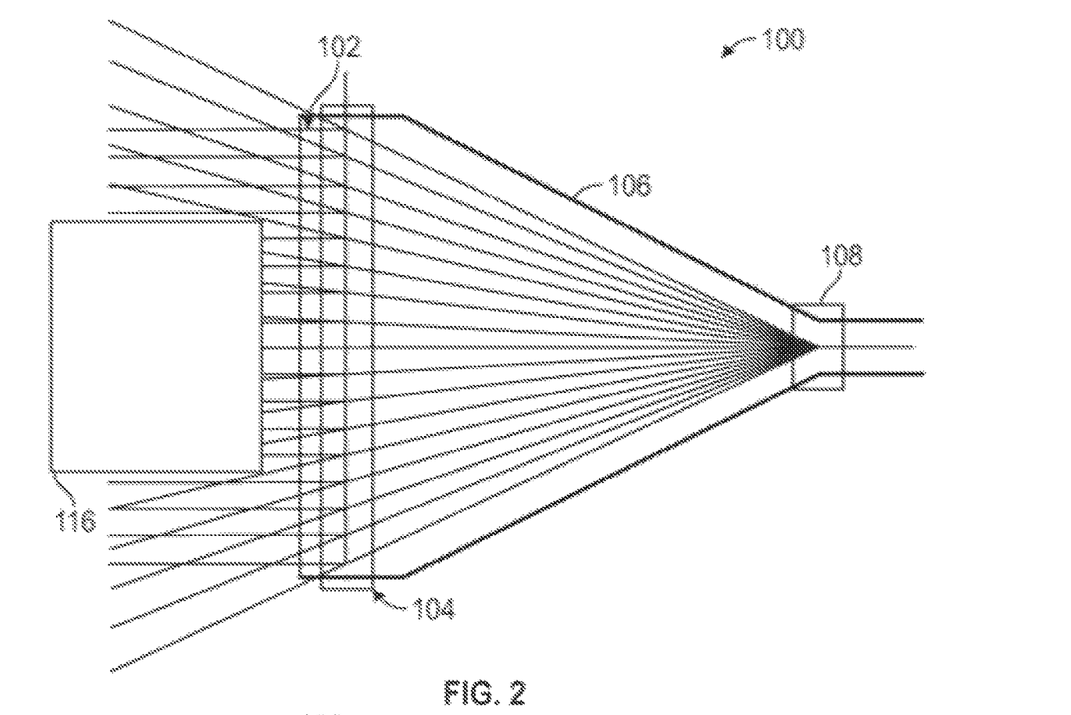
FIG. 2 illustrates a schematic diagram of a magnetic apparatus including divergent and parallel beams striking an irradiated object, in accordance with an embodiment.

FIG. 2 illustrates a schematic diagram of a magnetic apparatus 100 and divergent and parallel beams striking an irradiated object 116, in accordance with an embodiment. FIG. 2 compares the diverging beams (i.e., if there is no parallelizing array, and with the parallel beams if the array is present).

Figure 3:
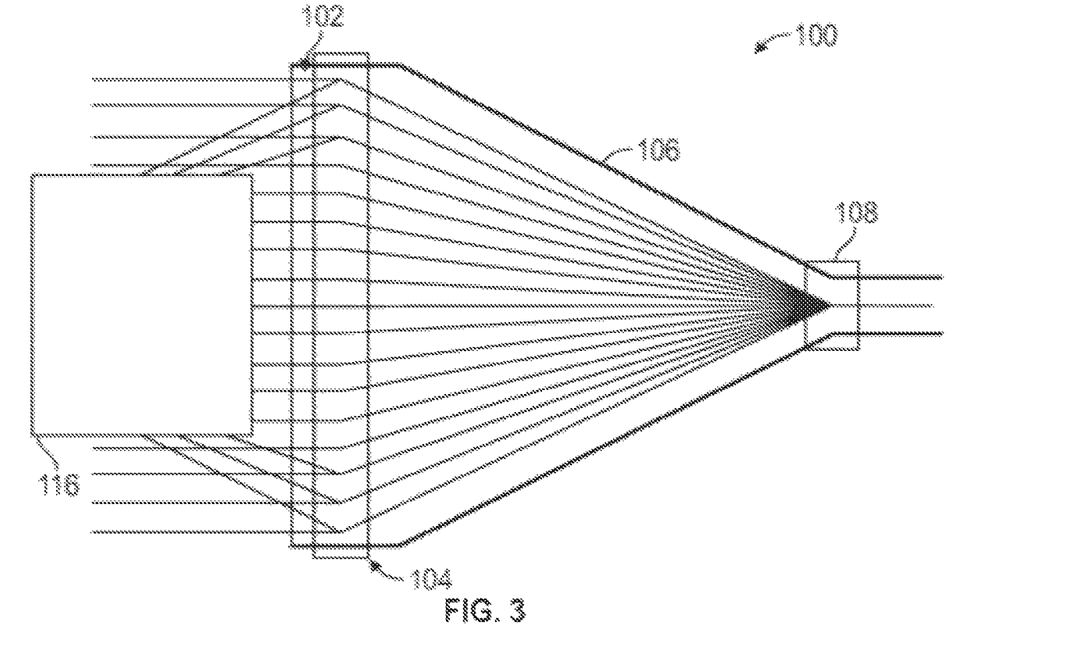
FIG. 3 illustrates a schematic diagram of a magnetic apparatus and parallelized beams and a combination of parallel and convergent beams, in accordance with an embodiment.
Figure 4:
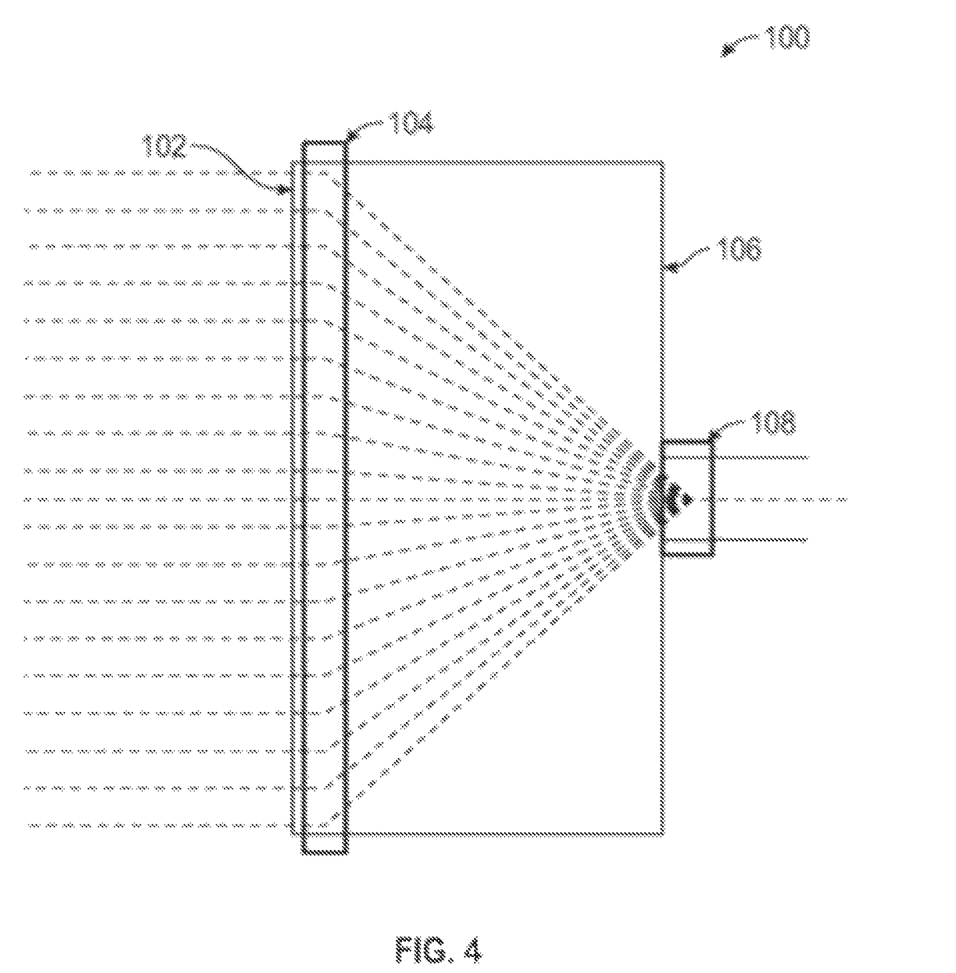
FIG. 4 illustrates a schematic diagram of a magnetic apparatus including divergent and parallel beams striking an irradiated object, in accordance with another embodiment.

FIG. 3, on the other hand, illustrates a schematic diagram of a magnetic apparatus 100 with respect to the irradiated object 116 and both parallelized beams and a combination of parallel and convergent beams. Note that in FIGS. 1-3, similar or identical parts or elements are indicated by identical reference numerals. FIG. 3 compares the parallel beams formed by the parallelizing array with a combination of parallel beams and converging beams on the outer portion. This may be desirable to create a more uniform distribution of dose in the product. This can be the result of a static configuration of the permanent magnets or the result of a mechanical system that may adjust the permanent magnet array in a dynamic manner.

FIG. 4 illustrates a schematic diagram of a magnetic apparatus 100 including divergent and parallel beams, in accordance with another embodiment. Note that in FIGS. 1-4, similar or identical parts or elements are indicated by identical reference numerals. A difference, however, between the configuration shown in FIG. 4 and FIGS. 1-3 is that the embodiment depicted in FIG. 4 depicts a vacuum chamber 106 that is rectangular or box-shaped rather than the triangular or horn-shaped vacuum chamber 106 depicted in FIGS. 1-3.

It can thus be appreciated that vacuum chamber configurations of varying size and shape can be implemented in accordance with the disclosed embodiments. In other words, the vacuum chamber 106 is not limited to only one particular size or shape but may be implemented in a variety of potential sizes and shapes. Thus, the first section 112 and the second section 114 discussed herein previously with respect to FIGS. 1-3 may not be necessary for the configuration shown in FIG. 4.

In addition, the scanning electromagnet 108 can be implemented in a configuration as part of the beam line 110 leading to a scanning horn. Alternatively, the scanning electromagnet 108 can be located just upstream of the horn assembly. In either case, it should be appreciated that the magnetic apparatus 100 is configured to parallelize any uniformly diverging beam.

The magnetic apparatus 100 can be used to produce scanning electron/Bremsstrahlung beams for use in various applications such as, for example, medical and pharmaceutical products sterilization, food and agricultural products radiation treatment, polymer composites manufacturing, electronic components processing, waste utilization, etc.

In certain embodiments, a scanning system is configured that moves the electron beam in a time-varying manner in a plane or over an area. For example, FIG. 5 illustrates a scanning system 500 further comprising a scanning RF cavity.

The apparatus 500 can be used to produce electron beams or X-rays for irradiation processes including, but not limited to industrial sterilization and other irradiation purposes. The apparatus 500 can include a scanning system 505 which can comprise a scanning radio frequency cavity (RF cavity) 515 and a vacuum chamber 510. An RF cavity creates an electric field that can alter the trajectory of a charged particle in the same manner that a magnetic field can alter the trajectory of a charged particle.

Note that in some example embodiments, the vacuum chamber 510 may be a cone-shaped vacuum chamber or a horn-shaped vacuum chamber referred to as a scanning horn vacuum chamber. It should be appreciated, however, that the vacuum chamber 510, although shown in FIGS. 1-3 as horn-shaped, is not limited to such a shape. Other configurations and shapes are possible. It is also possible, that in certain embodiments, a vacuum chamber may not be required, and the system could operate without a vacuum between scanning system and the magnet array.

Figure 5:
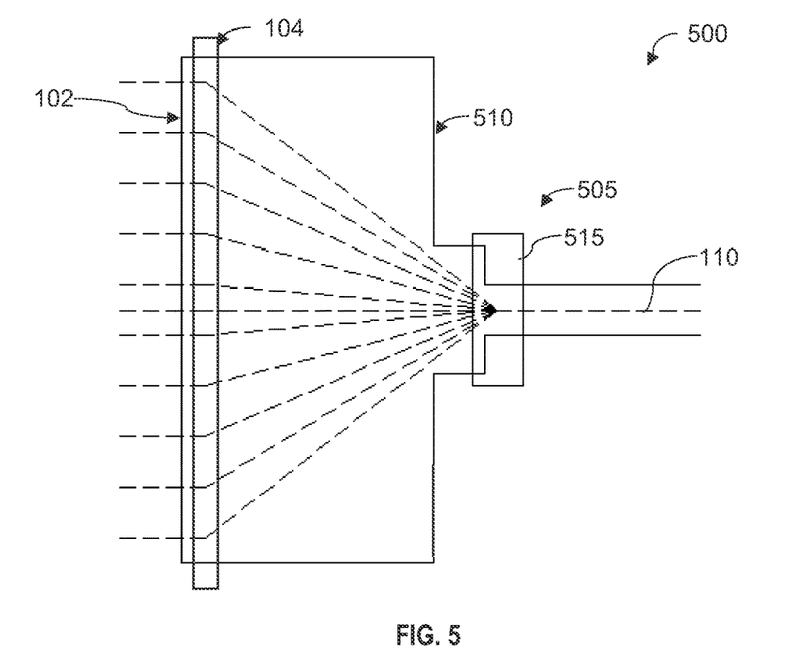
FIG. 5 illustrates a schematic diagram of a magnet apparatus with a scanning system, in accordance with the disclosed embodiments.

A beam line 110 is also depicted in FIG. 5 with respect to the scanning radio frequency cavity 515. A parallelizing permanent magnet array 104 is shown in FIG. 5 with respect to the vacuum chamber 510, and proximate to a target 102, which may be a Bremsstrahlung target or an object that is being irradiated. Note that in some embodiments, the target 102 can be located in a vacuum window if operating in an electron beam mode. The target 102 can also serve, in some example embodiments, as both a vacuum window and a Bremsstrahlung target if operating in an X-ray mode. In still other example embodiments, the vacuum window and Bremsstrahlung target can be separate components. If separate, this allows switching between electron beam and X-ray mode by moving the Bremsstrahlung target out of the way. Note that the parallelizing permanent magnet array 104 can be located within or outside the vacuum chamber 510. The scanning radio frequency cavity 515 creates a time-varying electric field that deflects the electron beam in a plane or over an area.

Figure 6A:
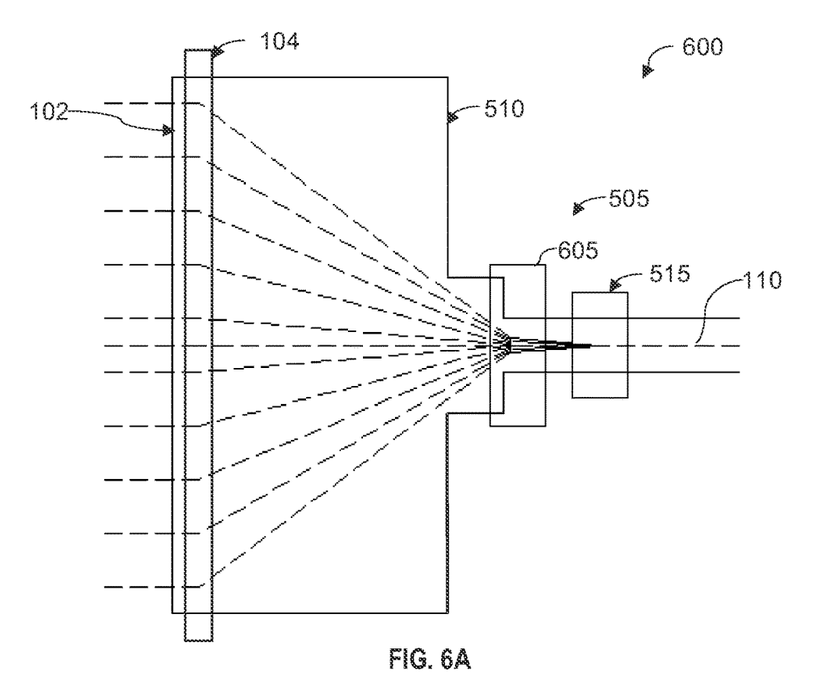
FIG. 6A illustrates a schematic diagram of a scanning system incorporating a gradient electromagnet, in accordance with the disclosed embodiments.

FIG. 6A illustrates an embodiment of an apparatus 600. The apparatus 600 comprises a scanning system 505, which can include a scanning RF cavity 515 coupled with a gradient electromagnet 605. A gradient electromagnet creates a magnetic field, which can be, but is not limited to, a quadrupole field, where the strength of the field is proportional to the distance from the central axis. The scanning RF cavity 515 can create a small deflection. The distance between the RF cavity and the gradient magnet is determined by parameters of the beam such that there is a maximum deflection at the gradient electromagnet 605. The gradient field of the electromagnet further deflects the beam depending on its distance from the central axis of the magnetic field. The time varying motion of the deflection by the RF cavity is then converted to a large deflection which can cover the extent of the parallelizing magnet 104 and vacuum window 102.

For example, for electron beams of certain energy levels, a scanning RF cavity may not provide electric fields strong enough to create the desired deflection. In such cases the scanning RF cavity 515 creates a small deflection which is then amplified by the gradient magnet 605 which is downstream of the RF cavity 515. The deflection experienced in the magnetic field of the gradient magnet 605 depends on the distance away from the central axis.

Figure 6B:
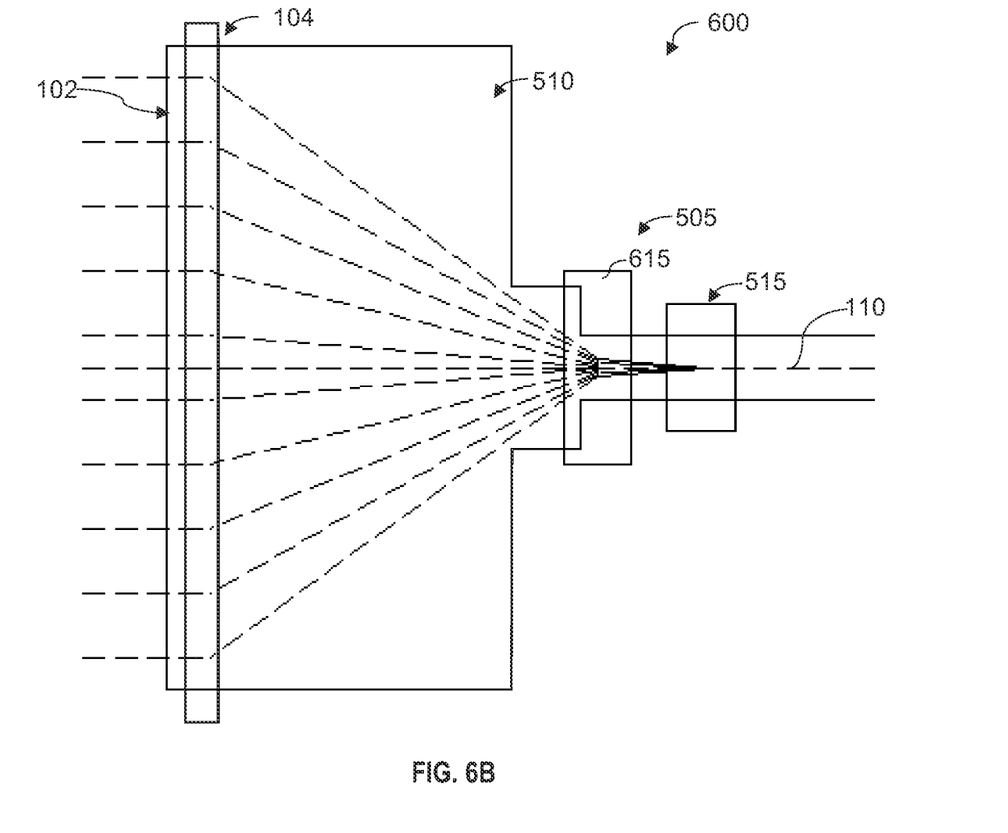
FIG. 6B illustrates a schematic diagram of a scanning system incorporating a gradient permanent magnet, in accordance with the disclosed embodiments.

FIG. 6B illustrates another embodiment of the apparatus 600. In this embodiment, the apparatus 600 comprises a scanning RF cavity 515 coupled with a gradient permanent magnet 615. The scanning RF cavity 515 can create a small deflection, which can be magnified by the gradient in the gradient permanent magnet 615 to move the beam in a time-varying manner in a plane. Again, when the scanning RF cavity does not provide electric fields strong enough to create the desired deflection, the scanning RF cavity 515 creates a small deflection which is then amplified by the gradient permanent magnet 615 which is downstream of the RF cavity 505. The distance between the RF cavity and the gradient magnet is determined by parameters of the beam such that there is a maximum deflection at the gradient electromagnet 605. The gradient field of the electromagnet further deflects the beam depending on its distance from the central axis of the magnetic field. The time varying motion of the deflection by the RF cavity is then converted to a large deflection which can cover the extent of the parallelizing magnet 104 and vacuum window 102.

The gradient in the permanent magnet 615 can be created using a magnet array. The magnet array can be produced by the construction of the permanent magnet material alone or in combination with ferrous metal pieces to smooth the gradient.

Figure 7:
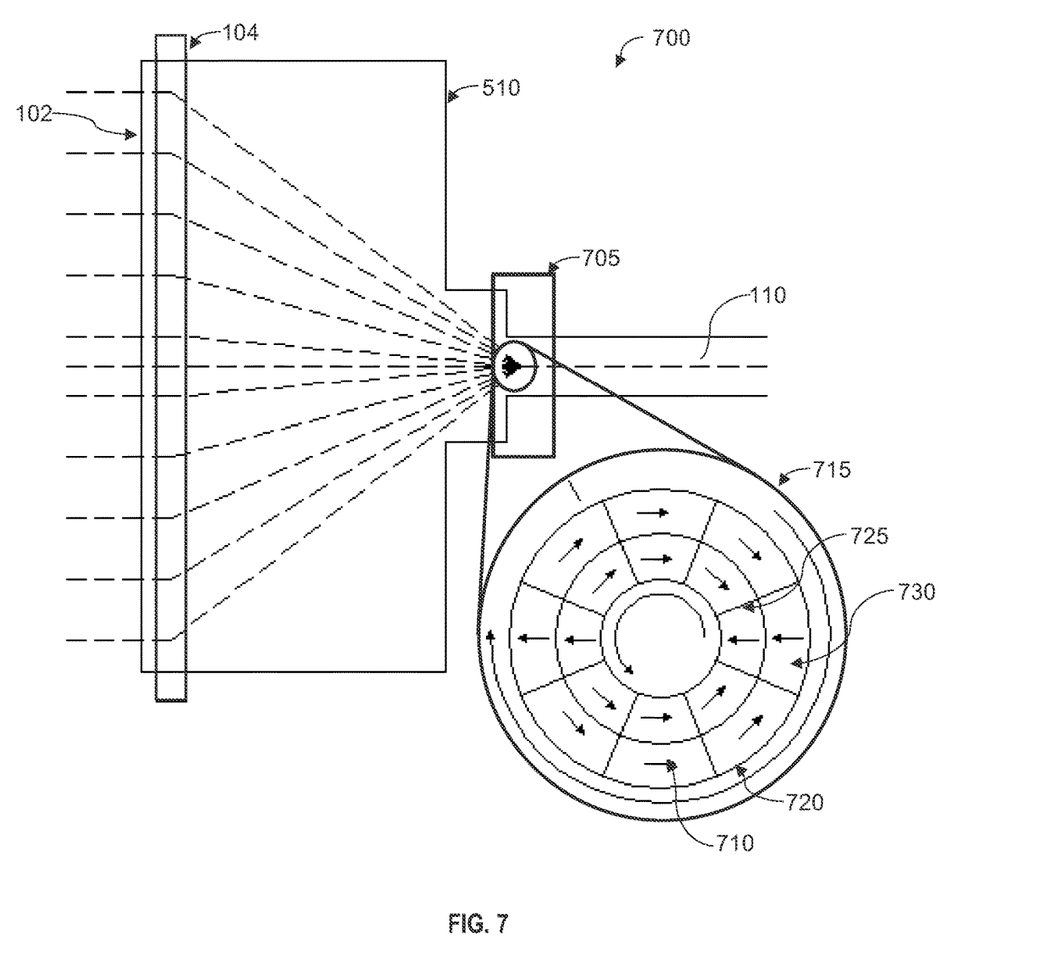
FIG. 7 illustrates a schematic diagram of a scanning system incorporating a permanent magnet with time-varying strength, in accordance with the disclosed embodiments.

FIG. 7 illustrates an embodiment of an apparatus 700. The apparatus comprises a time-varying permanent magnet scanning system 705. The time-varying permanent magnet scanning system 705 is illustrated in exploded view 715. An arrangement of permanent magnet pieces 710 can be configured on a base structure 720, which can be mechanically manipulated (e.g. rotated as shown by the arrows), create a varying superposition of magnetic fields in time to deflect the beam in a plane or over an area.

Referring to the exploded view, the inner ring 725 and outer ring 730 of permanent magnet material rotate in opposite directions. The respective rings can be driven by a motor. As shown, the magnetic field is maximum in the left direction. When the rings have each rotated 90 degrees in opposite directions, the fields from the inner ring of permanent magnets 725 and outer ring of permanent magnets 730 will cancel each other out and the resulting field will be zero. When they have rotated another 90 degrees, the field will be maximum in the right direction. This causes the electron beam to sweep up and down.

Figure 8A:
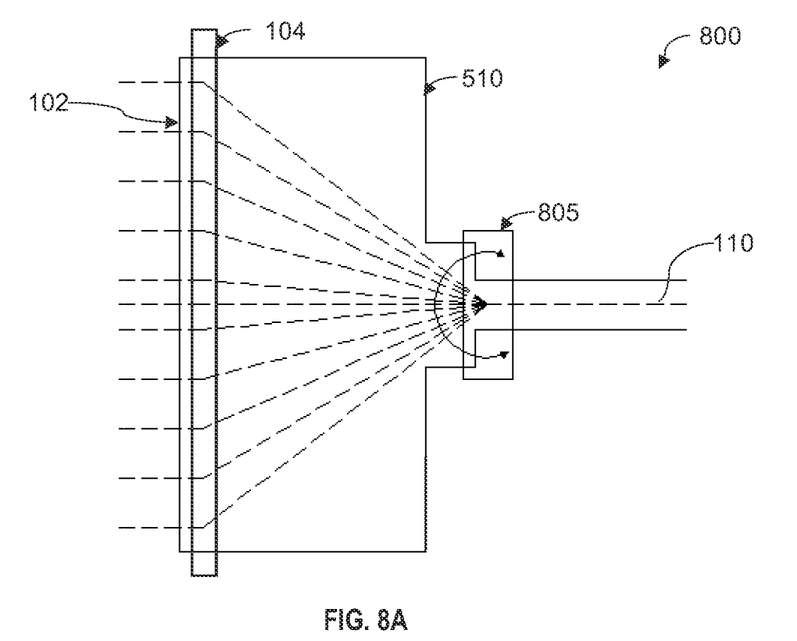
FIG. 8A illustrates a schematic diagram of a scanning system incorporating a time-varying electromagnet, in accordance with the disclosed embodiments.

In another embodiment, illustrated in FIG. 8A a time-varying electromagnet scanning system 800 is illustrated. In this embodiment, the electromagnet has a fixed strength but physically moves to sweep the electron beam. In the time-varying electromagnet scanning system, a constant gradient electromagnet 805 can be physically moved to deflect a stationary electron beam in a time-varying manner to deflect the beam in a plane or over an area. Here the electromagnet 805 provides a constant magnetic field and is physically rotated back and forth to sweep the beam. This movement can be provided by linear actuators, rocker arms, and rotating motors connected to linear guides.

Figure 8B:
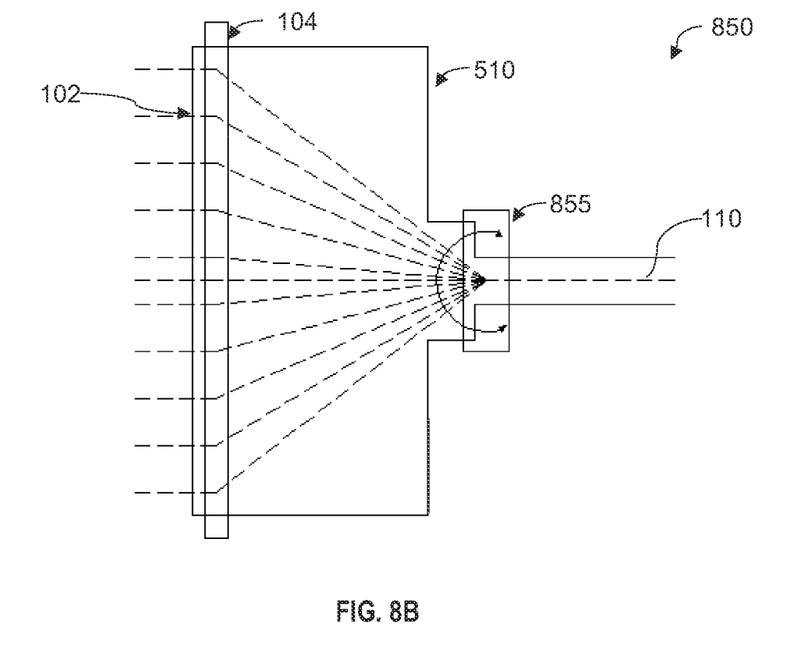
FIG. 8B illustrates a schematic diagram of a scanning system incorporating a time-varying permanent magnet, in accordance with the disclosed embodiments.

FIG. 8B illustrates a time-varying permanent magnet scanning system 850. In this embodiment, the permanent magnet has a fixed strength but physically moves to sweep the electron beam. In the time varying permanent magnet scanning system 850, a constant gradient permanent magnet array 855 can be physically moved to deflect a stationary electron beam in a time-varying manner to deflect the beam in a plane or over an area. Thus, the power supply for the magnet can be constant. A motor mechanism can be used to physically sweep the magnet as opposed to the magnet power supply producing a time varying output to change the strength of the magnetic field.

Figure 9:
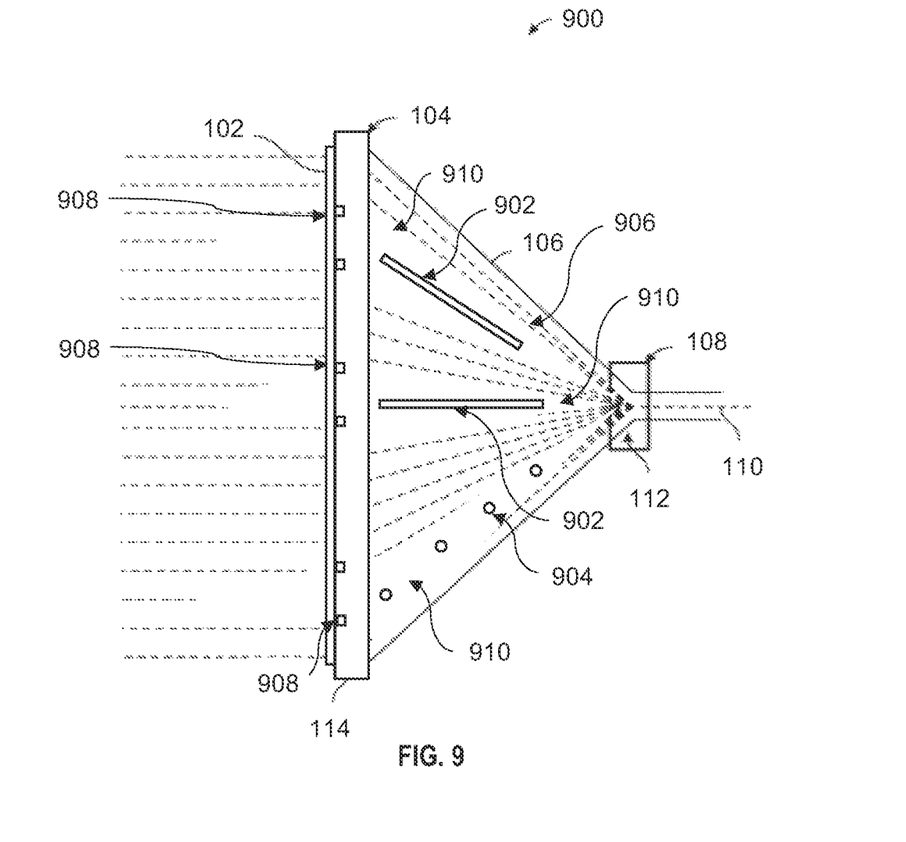
FIG. 9 illustrates a schematic diagram of a magnetic apparatus with an internally supported vacuum chamber, in accordance with an embodiment.

It is noteworthy that, the surface area and volume of the vacuum chambers disclosed herein make the structural requirements significant, particularly if the structure is externally supported. In certain embodiments, the structure can be internally braced. FIG. 9, illustrates a schematic diagram of an exemplary magnetic apparatus 900 used to irradiate an object. Note that in FIGS. 1-3 and 9, similar or identical parts or elements are indicated by identical reference numerals.

As illustrated in FIG. 9, the system 900 includes a scanning electromagnet 108 and vacuum chamber 106, parallelizing magnet array 104, and target 102. In this embodiment, internal bracing support elements 906 include discrete posts 902 and/or webs 904 can be used to lend structural support to the vacuum chamber 106. The posts 902 or webs can comprise beams or other such structural elements that are configured in the inner volume of the vacuum chamber 106 and affixed to the inner surface of the vacuum chamber 106.

By aligning the position of these support elements 906, the electron beam can be made to avoid striking them. As the beam is scanned by the scanning system 108, the accelerator (or the radio frequency of the accelerator) can be paused for the period of time when the beam would be directed at the support elements 906, creating voids 910 in the associated field.

By preventing the beam from hitting the support elements 906, the associated heat generated by the beam striking the structural elements (which would then have to be dissipated) can be reduced. This technique also eliminates resulting inefficiency (since this beam would not effectively reach the object of the irradiation) and reduces the production of unwanted radiation (which influences radiation shielding requirements and personnel protection).

To fill in the gaps 910 in the radiation field at the intended point of irradiation, the pole pieces 908 of the parallelizing magnets 104 can be shaped to direct the electron beam to fill in the gaps, since the strength of the magnetic field at any point is position dependent. The pole pieces 908 can incorporate dipole, quadrupole, sextupole, or any other magnetic field components to provide a uniform irradiation field, or tailored irradiation field according to the desired field.

It should be appreciated that the aforementioned embodiments can be used to create a time-varying sweep of an electron beam in a plane or over an area. The embodiments can be used with a Bremsstrahlung target downstream of the sweeping mechanism to create a time-varying sweep of an x-ray beam in a plane or over an area. In other embodiments, the systems can be used a vacuum chamber to transport the deflected electron beam to a reparallelizing permanent magnet horn with or without a Bremsstrahlung target downstream of the parallelizing system, or a Bremsstrahlung target without the parallelizing system.

Based on the foregoing, it can be appreciated that a number of example embodiments, preferred and alternative, are disclosed herein. For example, in a preferred embodiment, a magnetic apparatus can be implemented, which includes a scanning electromagnet that redirects a beam of charged particles; a vacuum chamber that prevents the atmosphere from interfering with the charged particles; and a parallelizing permanent magnet array for parallelizing the beam of charged particles including any uniformly diverging beam, wherein the parallelizing permanent magnet array is located proximate to a target comprising a Bremsstrahlung target or an object that is being irradiated and is further located within or outside the vacuum chamber, wherein a magnetic field of the scanning electromagnet is variable to produce all angles necessary to sweep the beam of charged particles across the target and wherein the parallelizing permanent magnet array is configured from a magnetic material that does not require an electric current.

In another embodiment, the beam of charged particles can be redirected by the parallelizing permanent magnet array from a diverging pattern output from the scanning electromagnet to a parallel pattern after being subjected to the parallelizing permanent magnet array.

In another embodiment, the beam of charged particles can comprise an electron beam.

In another embodiment, the beam of charged particles can comprise an optional X-ray portion after the beam of charged particles has been subject to parallelization.

In another embodiment, the parallelizing permanent magnet array can comprise a plurality of permanent magnets, wherein the plurality of permanent magnets is adjustable to compensate for a degradation of magnetic field strength over time.

In another embodiment, magnetic field strength can remain constant over a period of time by adjusting a gap between magnetic pole faces of permanent magnets among the plurality of permanent magnets.

In another embodiment, the magnetic field strength can be adjustable by at least one of: adjusting a gap between at least two poles of permanent magnets in the plurality of permanent magnets; or adding, removing or moving the magnetic material, which modifies the magnetic field of the permanent magnets, wherein the magnetic material is selected based on a magnetic permeability.

In another embodiment, the magnetic apparatus can comprise an irradiation device for irradiating an object.

In still another embodiment, the magnetic apparatus can include a scanning electromagnet that redirects a beam of charged particles; a vacuum chamber that prevents the atmosphere from interfering with the charged particles; and a parallelizing permanent magnet array for parallelizing the beam of charged particles including any uniformly diverging beam, wherein the parallelizing permanent magnet array is located proximate to a target comprising a Bremsstrahlung target or an object that is being irradiated and is further located within or outside the vacuum chamber, wherein a magnetic field of the scanning electromagnet is variable to produce all angles necessary to sweep the beam of charged particles across the target and wherein the parallelizing permanent magnet array is configured from a magnetic material that does not require an electric current, wherein the beam of charged particles is redirected by the parallelizing permanent magnet array from a diverging pattern output from the scanning electromagnet to a parallel pattern after being subjected to the parallelizing permanent magnet array.

In still another embodiment, a method of operating a magnetic apparatus, can involve redirecting a beam of charged particles with a scanning electromagnet that engages a vacuum chamber that prevents the atmosphere from interfering with the charged particles, and parallelizing the beam of charged particles including any uniformly diverging beam with a parallelizing permanent magnet array, wherein the parallelizing permanent magnet array is located proximate to a target comprising a Bremsstrahlung target or an object that is being irradiated and which is further located within or outside the vacuum chamber, wherein a magnetic field of the scanning electromagnet is variable to produce all angles necessary to sweep the beam of charged particles across the target and wherein the parallelizing permanent magnet array is configured from a magnetic material that does not require an electric current.

In another embodiment, the method of operating a magnetic apparatus can involve redirecting the beam of charged particles by the parallelizing permanent magnet array from a diverging pattern output from the scanning electromagnet to a parallel pattern after being subjected to the parallelizing permanent magnet array.

In another embodiment of the method of operating a magnetic apparatus, the beam of charged particles can comprise an electron beam.

In another embodiment of the method of operating a magnetic apparatus, the beam of charged particles can comprise an X-ray portion after the beam of charged particles has been subject to parallelization.

In another embodiment of the method of operating a magnetic apparatus, the parallelizing permanent magnet array can comprise a plurality of permanent magnets, wherein the plurality of permanent magnets is adjustable to compensate for a degradation of magnetic field strength over time.

In another embodiment of the method of operating a magnetic apparatus, the magnetic field strength can remain constant by adjusting a gap between magnetic pole faces of permanent magnets among the plurality of permanent magnets.

In another embodiment of the method of operating a magnetic apparatus the magnetic field strength can be adjustable by: adjusting a gap between at least two poles of permanent magnets in the plurality of permanent magnets, or adding, removing or moving the magnetic material, which modifies the magnetic field of the permanent magnets, wherein the magnetic material is selected based on a magnetic permeability.

In another embodiment of the method of operating a magnetic apparatus, the magnetic apparatus can comprise an irradiation device for irradiating an object.

It will be appreciated that variations of the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which are also intended to be encompassed by the following claims.

What is claimed is:

1. An apparatus, comprising:
   a magnet assembly that redirects a beam of charged particles;
   a vacuum chamber that prevents the atmosphere from interfering with the charged particles, the vacuum chamber comprising at least one internal bracing support element; and
   a parallelizing magnet array for parallelizing the beam of charged particles.

2. The apparatus of claim 1 wherein the beam of charged particles is redirected by the parallelizing magnet array from a diverging pattern output from the magnet assembly to a parallel pattern after being subjected to the parallelizing magnet array.

3. The apparatus of claim 1 wherein the beam of charged particles comprises an electron beam.

4. The apparatus of claim 1 wherein the at least one internal bracing support element comprises one of:
   a discrete post; and
   a web.

5. The apparatus of claim 1 wherein the parallelizing magnet array comprises a plurality of permanent magnets.

6. The apparatus of claim 5 wherein a magnetic field strength is controllable by adjusting a gap between magnetic pole faces of permanent magnets among the plurality of permanent magnets.

7. The apparatus of claim 1 wherein a magnetic field strength is adjustable by at least one of:
   adjusting a gap between at least two poles of permanent magnets in the plurality of permanent magnets; or
   adding, removing or moving magnetic material, which modifies the magnetic field of the permanent magnets.

8. The apparatus of claim 1 further comprising:
   at least one pole piece in the parallelizing magnet array configured to adjust the beam of charged particles into a uniform irradiation field.

9. A magnetic apparatus, comprising:
   a scanning magnetic assembly that redirects a beam of charged particles;
   a vacuum chamber that prevents the atmosphere from interfering with the charged particles, the vacuum chamber comprising at least one internal bracing support element; and
   a parallelizing permanent magnet array for parallelizing the beam of charged particles wherein the parallelizing permanent magnet array is located proximate to a target comprising a Bremsstrahlung target.

10. The magnetic apparatus of claim 9 wherein the scanning magnetic assembly comprises:
    a scanning RF cavity; and
    a magnetic gradient assembly coupled to the scanning RF cavity.

11. The magnetic apparatus of claim 10 wherein the magnetic gradient assembly further comprises one of:
    a gradient electromagnet; and
    a gradient permanent magnet.

12. The magnetic apparatus of claim 9 wherein the at least one internal bracing support element comprises one of:
    a discrete post; and
    a web.

13. A method, comprising:
    redirecting a beam of charged particles with a scanning system engaged to a vacuum chamber that prevents atmosphere from interfering with the charged particles;
    pausing the beam when it would be incident on an internal support structure;
    parallelizing the beam of charged particles with a parallelizing magnet array, wherein the parallelizing permanent magnet array is located proximate to a target; and
    sweeping the beam of charged particles across the target.

14. The method of claim 13 further comprising:
    redirecting the beam of charged particles by the parallelizing magnet array from a diverging pattern output from the scanning system to a parallel pattern after being subjected to the parallelizing magnet array.

15. The method of claim 13 wherein the beam of charged particles comprises an electron beam.

16. The method of claim 13 wherein the beam of charged particles comprises an X-ray portion after the beam of charged particles has been subject to parallelization.

17. The method of claim 13 wherein the parallelizing magnet array comprises a plurality of permanent magnets, wherein the plurality of permanent magnets is adjustable to compensate for a degradation of magnetic field strength over time.

18. The method of claim 17 further comprising:
    adjusting field strength by adjusting a gap between magnetic pole faces of permanent magnets among the plurality of permanent magnets.

19. The method of claim 17 wherein magnetic field strength is adjustable by:
    adjusting a gap between at least two poles of permanent magnets in the plurality of permanent magnets; or
    adding, removing or moving magnetic material associated with the plurality of permanent magnets.

20. The method of claim 13 wherein the magnetic apparatus comprises an irradiation device for irradiating an object.

* * * * *